(12) United States Patent
Hong et al.

(10) Patent No.: US 8,124,054 B2
(45) Date of Patent: Feb. 28, 2012

(54) CHELATING AGENT CONJUGATED α-MSH PEPTIDE DERIVATIVES, PREPARATION METHOD THEREOF AND COMPOSITION FOR DIAGNOSIS AND TREATMENT OF MELANOMA COMPRISING THE SAME AS AN ACTIVE INGREDIENT

(75) Inventors: Young-Don Hong, Daejeon (KR); Sun-Ju Choi, Daejeon (KR); So-Young Lee, Daejeon (KR); Kang-Hyuk Choi, Daejeon (KR)

(73) Assignee: Korea Atomic Energy Research Institute, Daejeon (KR)

( * ) Notice: Subject to any disclaimer, the term of this patent is extended or adjusted under 35 U.S.C. 154(b) by 359 days.

(21) Appl. No.: 12/409,288

(22) Filed: Mar. 23, 2009

(65) Prior Publication Data

US 2009/0304586 A1    Dec. 10, 2009

(30) Foreign Application Priority Data

Mar. 26, 2008   (KR) .................. 10-2008-0027878

(51) Int. Cl.
*A61K 51/00* (2006.01)
*A61M 36/14* (2006.01)

(52) U.S. Cl. .............. 424/1.69; 424/1.11; 424/1.65; 514/10.7

(58) Field of Classification Search .......... 424/1.11, 424/1.65, 1.81, 1.85, 1.89, 9.1, 9.3, 9.4, 9.5, 424/9.6, 9.7, 9.8, 1.69; 530/300, 312, 330; 534/7, 10–16; 514/1.1, 10.7
See application file for complete search history.

(56) References Cited

U.S. PATENT DOCUMENTS 7,405,194 B2   7/2008  Olson et al.
7,419,957 B2   9/2008  Hwu et al.

FOREIGN PATENT DOCUMENTS

WO    WO 00/12762    3/2000

OTHER PUBLICATIONS

Bard et al (Br. J. Cancer, 1990, vol. 62, pp. 919-922).*
Wei et al. ( 2007) "Synthesis and Biologic Evaluation of $^{64}$Cu-Labeled Rhenium-Cyclized α-MSH Peptide Analog Using a Cross-Bridged Cyclam Chelator," The Journal of Nuclear Medicine, 48(1):64-72.

* cited by examiner

*Primary Examiner* — D L Jones
(74) *Attorney, Agent, or Firm* — Greenlee Sullivan P.C.

(57) ABSTRACT

Disclosed are chelating agent-conjugated α-MSH peptide derivatives, preparation methods thereof, and compositions for use in a diagnosis or treatment of a melanoma tumor containing the same as an active ingredient. The novel α-MSH peptide derivatives conjugated with chelating agent according to the present invention are highly selective to the melanocortin-1 receptor which is α-MSH receptor expressing in melanoma tumor and their labeling rate of a radioactive isotope is high. Also, they remain in kidney shortly and have high taking rate of the melanoma tumor. Therefore, with the aforesaid reasons, they may be effectively used for early diagnosis or treatment of melanoma tumor.

11 Claims, 7 Drawing Sheets

|   | RT | Area | % Area | Height |
|---|------|---------|--------|--------|
| 1 | 3.703 | 70192 | 0.77 | 7341 |
| 2 | 16.373 | 9026191 | 99.23 | 519858 |

|   | RT | Area | % Area | Height |
|---|---|---|---|---|
| 1 | 8.886 | 19939502 | 100.00 | 1008775 |

|   | RT    | Area     | % Area | Height |
|---|-------|----------|--------|--------|
| 1 | 2.551 | 200600   | 1.52   | 21045  |
| 2 | 9.626 | 12988476 | 98.48  | 304633 |

|   | RT | Area | % Area | Height |
|---|---|---|---|---|
| 1 | 9.659 | 9276367 | 100.00 | 561052 |

SEQUENCE LISTING

```
<160> NUMBER OF SEQ ID NOS: 8

<210> SEQ ID NO 1
<211> LENGTH: 8
<212> TYPE: PRT
<213> ORGANISM: Artificial Sequence
<220> FEATURE:
<223> OTHER INFORMATION: Synthetic construct: alpha-MSH peptide
      derivative 1
<220> FEATURE:
<221> NAME/KEY: MISC_FEATURE
<222> LOCATION: (2)..(2)
<223> OTHER INFORMATION: Xaa at position 2 is diaminopropionic acid
      (Dap)
<220> FEATURE:
<221> NAME/KEY: MISC_FEATURE
<222> LOCATION: (5)..(5)
<223> OTHER INFORMATION: Xaa at position 5 is dPhe
<220> FEATURE:
```

```
<221> NAME/KEY: MOD_RES
<222> LOCATION: (8)..(8)
<223> OTHER INFORMATION: Asp at position 8, in certain instances has a
      c-terminal amide (rather than a carboxyl group)

<400> SEQUENCE: 1

Gly Xaa Glu His Xaa Arg Trp Asp
1               5

<210> SEQ ID NO 2
<211> LENGTH: 11
<212> TYPE: PRT
<213> ORGANISM: Artificial Sequence
<220> FEATURE:
<223> OTHER INFORMATION: Synthetic construct: alpha-MSH peptide
      derivative 2
<220> FEATURE:
<221> NAME/KEY: MOD_RES
<222> LOCATION: (1)..(1)
<223> OTHER INFORMATION: Gly at position 1, in certain instances, is
      conjugated to a 1,4,7,10-tetrazacyclododecane-1,4,7,10-tetraacetic
      acid or diethyleneatriaminepentaacetic acid
<220> FEATURE:
<221> NAME/KEY: MISC_FEATURE
<222> LOCATION: (2)..(2)
<223> OTHER INFORMATION: Xaa at position 2 is diaminopropionic acid
      (Dap)
<220> FEATURE:
<221> NAME/KEY: MISC_FEATURE
<222> LOCATION: (5)..(5)
<223> OTHER INFORMATION: Xaa at position 5 is dPhe
<220> FEATURE:
<221> NAME/KEY: MOD_RES
<222> LOCATION: (11)..(11)
<223> OTHER INFORMATION: Val at position 11, in certain instances has an
      amide rather than a C-terminal carboxyl group

<400> SEQUENCE: 2

Gly Xaa Glu His Xaa Arg Trp Asp Lys Pro Val
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Synthetic construct: alpha-MSH peptide
      derivative 3
<220> FEATURE:
<221> NAME/KEY: MISC_FEATURE
<222> LOCATION: (2)..(2)
<223> OTHER INFORMATION: Xaa at position 2 is diaminopropionic acid
<220> FEATURE:
<221> NAME/KEY: MISC_FEATURE
<222> LOCATION: (5)..(5)
<223> OTHER INFORMATION: Xaa at position 5 is dPhe
<220> FEATURE:
<221> NAME/KEY: MOD_RES
<222> LOCATION: (11)..(11)
<223> OTHER INFORMATION: Val at position 11, in certain instances, has a
      C-terminal amide rather than a carboxyl group

<400> SEQUENCE: 3

Gly Xaa Glu His Xaa Arg Trp Asp Arg Pro Val
1               5                   10

<210> SEQ ID NO 4
<211> LENGTH: 8
<212> TYPE: PRT
<213> ORGANISM: Artificial Sequence
<220> FEATURE:
<223> OTHER INFORMATION: Synthetic construct: alpha-MSH peptide
      derivative 4
<220> FEATURE:
```

```
<221> NAME/KEY: MISC_FEATURE
<222> LOCATION: (2)..(2)
<223> OTHER INFORMATION: Xaa at position 2 is diaminopropionic acid
<220> FEATURE:
<221> NAME/KEY: MISC_FEATURE
<222> LOCATION: (5)..(5)
<223> OTHER INFORMATION: Xaa at position 5 is dPhe
<220> FEATURE:
<221> NAME/KEY: MOD_RES
<222> LOCATION: (8)..(8)
<223> OTHER INFORMATION: Asp at position 8, in certain instances, has a
      C-terminal amide rather than a carboxyl group

<400> SEQUENCE: 4

Gly Xaa Gln His Xaa Arg Trp Asp
1               5

<210> SEQ ID NO 5
<211> LENGTH: 11
<212> TYPE: PRT
<213> ORGANISM: Artificial Sequence
<220> FEATURE:
<223> OTHER INFORMATION: Synthetic construct: alpha-MSH peptide
      derivative 5
<220> FEATURE:
<221> NAME/KEY: MISC_FEATURE
<222> LOCATION: (2)..(2)
<223> OTHER INFORMATION: Xaa at position 2 is diaminopropionic acid
<220> FEATURE:
<221> NAME/KEY: MISC_FEATURE
<222> LOCATION: (5)..(5)
<223> OTHER INFORMATION: Xaa at position 5 is dPhe
<220> FEATURE:
<221> NAME/KEY: MOD_RES
<222> LOCATION: (11)..(11)
<223> OTHER INFORMATION: Val at position 11, in certain instances, has a
      C-terminal amide rather than a carboxyl group

<400> SEQUENCE: 5

Gly Xaa Gln His Xaa Arg Trp Asp Lys Pro Val
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Synthetic construct: alpha-MSH peptide
      derivative 6
<220> FEATURE:
<221> NAME/KEY: MISC_FEATURE
<222> LOCATION: (2)..(2)
<223> OTHER INFORMATION: Xaa at position 2 is diaminopropionic acid
<220> FEATURE:
<221> NAME/KEY: MISC_FEATURE
<222> LOCATION: (5)..(5)
<223> OTHER INFORMATION: Xaa at position 5 is dPhe
<220> FEATURE:
<221> NAME/KEY: MOD_RES
<222> LOCATION: (11)..(11)
<223> OTHER INFORMATION: Val at position 11, in certain instances, has a
      C-terminal amide rather than a carboxyl group

<400> SEQUENCE: 6

Gly Xaa Gln His Xaa Arg Trp Asp Arg Pro Val
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Synthetic construct: partial sequence of
      certain alpha-MSH peptide derivatives, may be in straight or
```

```
        cyclic form
<220> FEATURE:
<221> NAME/KEY: MISC_FEATURE
<222> LOCATION: (1)..(1)
<223> OTHER INFORMATION: Xaa at position 1 is diaminopropionic acid
<220> FEATURE:
<221> NAME/KEY: MISC_FEATURE
<222> LOCATION: (4)..(4)
<223> OTHER INFORMATION: Xaa at position 4 is dPhe

<400> SEQUENCE: 7

Xaa Glu His Xaa Arg Trp Asp
1               5

<210> SEQ ID NO 8
<211> LENGTH: 4
<212> TYPE: PRT
<213> ORGANISM: Artificial Sequence
<220> FEATURE:
<223> OTHER INFORMATION: Synthetic construct: tetrapeptide of alpha-MSH
      known to play crucial role in recognizing receptor

<400> SEQUENCE: 8

His Phe Arg Trp
1
```

CHELATING AGENT CONJUGATED α-MSH PEPTIDE DERIVATIVES, PREPARATION METHOD THEREOF AND COMPOSITION FOR DIAGNOSIS AND TREATMENT OF MELANOMA COMPRISING THE SAME AS AN ACTIVE INGREDIENT

CROSS-REFERENCE TO RELATED APPLICATION

This application claims priority to Korean Patent Application No. 10-20088-027878 filed Mar. 26, 2008 which is incorporated herein by reference to the extent not inconsistent herewith.

BACKGROUND OF THE INVENTION

1. Field of the Invention

The present invention relates generally to a chelating agent-conjugated α-melanocyte stimulating hormone peptide derivative, a method for the preparation thereof, and a composition for the diagnosis and treatment of melanoma comprising the same as an active ingredient.

2. Description of the Related Art

Among various skin cancers, malignant melanoma is the most dangerous type, leading to the highest mortality. A malignant tumor of melanocytes, that is, pigment-producing cells, or a nevocellular nevus is called melanoma.

In Korea, about 1~1.5 cases of melanoma are diagnosed per 100,000 persons each year, with the morbidity increasing annually. According to a recent survey, melanoma occurs slightly more frequently in females, with a prevalence rate of 51.3%, than in males, with a prevalence rate of 48.7%. Melanoma occurs at a low rate in people under 20 years of age, but sharply increases in incidence rate among people in their forties or higher. The old, aged seventy or above, frequently suffer from melanoma. It is known that persons with lower degrees of skin pigmentation or with higher intensity or longer duration of sun exposure have a significantly greater risk for melanoma. Mutations in the cell cycle regulation genes, CDKN2A and CDK4, have been reported to increase the genetic susceptibility to melanoma tenfold.

Despite many years of intensive laboratory and clinical research, the surgical resection of primary tumors is the sole and effective cure developed to date. A number of debates have been made on sentinel lymph node biopsy for the treatment and metastatic prevention of melanoma. Additionally, an NMR spectrometer has been used for diagnosis and operation of metastasized sites. Such post-operation supplementary methods have made little progress thus far. Vaccines or cytokines have also been employed, but the use thereof in treatment has progressed only a little.

As mentioned above, melanoma can be completely cured if it is found in an early stage. If not found immediately, it rapidly spreads to other healthy parts of the body, along the lymph glands. Once they have spread, the cancer cells are hard to control. Accordingly, it is very important to find primary melanoma tumors and metastasized sites.

As it is known that current therapy is insufficient to increase the survival of patients of metastasized melanoma, intensive attention is now being paid to therapeutic agents that can effectively image melanoma tumors and take advantage of the energy emitted from radio isotopes.

Radio isotope-conjugated antibodies or antibody fragments are currently difficult to apply to the treatment of melanoma, not only because antibodies that can target melanoma-associated antigens have not yet been found, but also because antibodies under clinical and laboratory study show low tumor uptake rates and slow emission of radioisotopes from tumors. However, the finding that the melanocortin-1 receptor (MC1-R), an α-melanocyte stimulating hormone (hereinafter referred to as "α-MSH") receptor, is expressed in human and murine melanocytes allows for various research on the image diagnosis and treatment of melanoma with radiolabeled α-MSH derivatives [Wei L, at al., J. Nucl. Med. 2007: 48: 64-72].

α-MSH is a tridecapeptide which is a class of peptide hormones produced by cells in the intermediate lobe of the pituitary gland. Of the amino acid sequence of α-MSH, the tetrapeptide His-Phe-Arg-Trp (SEQ ID NO: 8) is known to play a crucial role in recognizing the receptor, as analyzed with structure-bioactivity relationship. α-MSH is also known to increase about 1,500 times in binding affinity for the receptor when the Phe residue is modified into D-form-Phe.

In spite of the observation of the tumor uptake of radiolabeled α-MSH in animal models, they are limitedly used in practice due to the high renal retention and low tumor uptake thereof.

Leading to the present invention, intensive and thorough research on the diagnosis and treatment of primary melanoma, conducted by the present inventors, resulted in the finding that the conjugation of a chelating agent with α-MSH allows the α-MSH to be more selective for the melanocortin-1 receptor, remain in the kidney for a shorter period of time, and increase in tumor uptake.

SUMMARY OF THE INVENTION

Accordingly, the present invention has been made keeping in mind the above problems occurring in the prior art, and an object of the present invention is to provide a chelating agent-conjugated α-MSH peptide derivative that can be labeled with a radioisotope at a high yield and shows high tumor uptake.

It is another object of the present invention to provide a method for the preparation of the chelating agent-conjugated α-MSH peptide derivative.

It is a further object of the present invention to provide a radiolabeled chelating agent-conjugated α-MSH peptide derivative.

It is still a further object of the present invention to provide a method for the preparation of the radiolabeled chelating agent-conjugated α-MSH peptide derivative.

It is still another object of the present invention to provide a composition for the diagnosis of melanoma, which is specific for melanoma.

It is yet another object of the present invention to provide a composition for the treatment of melanoma, which shows a high therapeutic effect.

In order to accomplish these objects, a chelating agent-conjugated α-MSH peptide derivative is provided, wherein a chelating agent selected from a group consisting of 1,4,7,10-tetrazacyclododecane-1,4,7,10-tetraacetic acid (DOTA) and diethylenetriaminepentaacetic acid (DTPA) is conjugated with an α-MSH peptide derivative, which is based on an amino acid sequence selected from a group consisting of:

(SEQ ID NO: 1)
1)  Gly-Dap-Glu-His-dPhe-Arg-Trp-Asp-CONH$_2$;

(SEQ ID NO: 2)
2)  Gly-Dap-Glu-His-dPhe-Arg-Trp-Asp-Lys-Pro-Val-CONH$_2$;

-continued

```
                                              (SEQ ID NO: 3)
3)  Gly-Dap-Glu-His-dPhe-Arg-Trp-Asp-Arg-Pro-Val-
    CONH2;

(SEQ ID NO: 4)
4)  Gly-Dap-Gln-His-dPhe-Arg-Trp-Asp-CONH2;

(SEQ ID NO: 5)
5)  Gly-Dap-Gln-His-dPhe-Arg-Trp-Asp-Lys-Pro-Val-
    CONH2;
    and (SEQ ID NO: 6)
6)  Gly-Dap-Gln-His-dPhe-Arg-Trp-Asp-Arg-Pro-Val-
    CONH2.
```

Also, there is provided a method for preparing a chelating agent-conjugated α-MSH peptide derivative, comprising: synthesizing an α-MSH peptide derivative through amino acid coupling reactions; conjugating the α-MSH peptide derivative with a chelating agent to form a conjugate; and deprotecting the conjugate.

Also, there is provided a radiolabeled chelating agent-conjugated α-MSH peptide derivative, wherein the chelating agent-conjugate α-MSH peptide derivative is labeled with a radioisotope. Preferably, the radioisotope is selected from a group consisting of Sc-47, Cu-64, Cu-67, Ga-67, Ga-68, Y-86, Y-90, Tc-99m, In-111, Pm-149, Sm-153, Dy-165, Ho-166, Er-169, Lu-177, Re-186, Re-188 and Bi-212.

Also, there is provided a method for preparing the radiolabeled chelating agent-conjugated α-MSH peptide derivative, comprising reacting the chelating agent-conjugated α-MSH peptide derivative with a radioisotope in the presence of a stabilizer.

Also, a composition comprising the radiolabeled chelating agent-conjugated α-MSH peptide derivative as an active ingredient is provided for the diagnosis of melanoma.

Also, a composition comprising the radiolabeled chelating agent-conjugated α-MSH peptide derivative as an active ingredient is provided for the treatment of melanoma.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Figure 1:
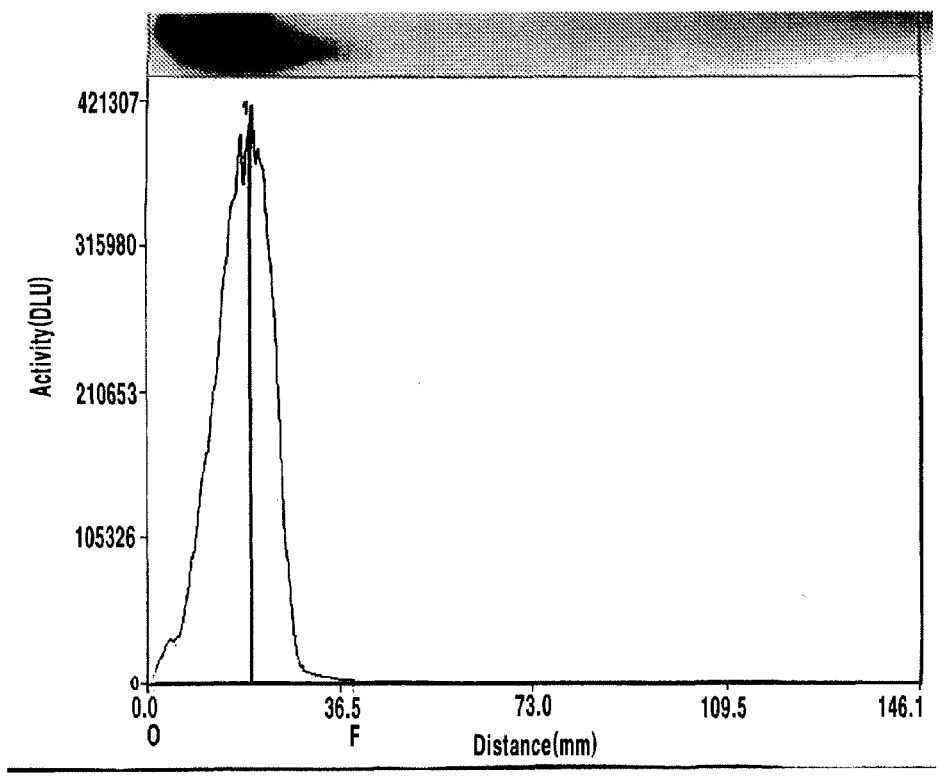
FIG. 1 shows a TLC chromatogram of a radiolabeled chelating agent-conjugated α-MSH peptide derivative according to an embodiment of the present invention.

In accordance with an aspect thereof, the present invention provides a chelating agent-conjugated α-MSH peptide derivative.

In the chelating agent-conjugated α-MSH peptide derivative, the chelating agent is preferably 1,4,7,10-tetrazacyclododecane-1,4,7,10-tetraacetic acid (DOTA), but is not limited thereto. Once it has been labeled with metal radioisotopes, the DOTA chelating agent is unlikely to separate therefrom for a long period of time. Also, the radiolabeled DOTA chelating agent complex is highly stable, as assayed at a high temperature (90° C.), for stability on radiolabeled DOTA-conjugated α-MSH peptide derivative.

Instead of DOTA, other chelating agents may be used in the present invention.

Examples of the chelating agent useful in the present invention include DOTA, diethylene triaminepentaacetic acid (DTPA), 1,4,7-triazacyclononane-1,4,7-triacetic acid (NOTA), triethylene tetraamine (TETA) or deferoxamine (DFO), with preference for DOTA and DTPA.

In order to increase the binding affinity of the chelating agent-conjugated α-MSH peptide derivative according to the present invention for the melanocortin-1 receptor, the α-MSH peptide derivative of the present invention preferably comprise an amino acid sequence selected from a group consisting of:

```
                                              (SEQ ID NO: 1)
1)  Gly-Dap-Glu-His-dPhe-Arg-Trp-Asp-CONH2;

(SEQ ID NO: 2)
2)  Gly-Dap-Glu-His-dPhe-Arg-Trp-Asp-Lys-Pro-Val-
    CONH2;

(SEQ ID NO: 3)
3)  Gly-Dap-Glu-His-dPhe-Arg-Trp-Asp-Arg-Pro-Val-
    CONH2;

(SEQ ID NO: 4)
4)  Gly-Dap-Gln-His-dPhe-Arg-Trp-Asp-CONH2;

(SEQ ID NO: 5)
5)  Gly-Dap-Gln-His-dPhe-Arg-Trp-Asp-Lys-Pro-Val-
    CONH2;
    and (SEQ ID NO: 6)
6)  Gly-Dap-Gln-His-dPhe-Arg-Trp-Asp-Arg-Pro-Val-
    CONH2.
```

The partial amino sequence Dap-Glu-His-dPhe-Arg-Trp-Asp (SEQ ID NO: 7) may be in a straight or cyclic form.

In accordance with another aspect thereof, the present invention provides a method for preparing the chelating agent-conjugated α-MSH peptide derivative.

According to the method, the chelating agent-conjugated α-MSH peptide derivative can be prepared by:

Synthesizing an α-MSH peptide derivative (Step 1);
Conjugating the α-MSH peptide derivative synthesized in Step 1 with a chelating agent (Step 2); and
Deprotecting the resulting conjugate (Step 3).

Below, a detailed description is given of the preparation method.

First, an α-MSH peptide derivative is synthesized in Step 1. The synthesis of α-MSH peptide derivative may be achieved using a method well known in the art, and preferably through an amino acid coupling reaction.

An illustrative and non-limiting example of the amino acid coupling reaction is the use of $NH_2$-MBHA resin on which the peptide chain is assembled in the presence of excess HOBt, HBTU, DIPEA and $N^\alpha$-Fmoc in dimethylformamide (hereinafter referred to as "DMF") as a solvent.

Next, the α-MSH peptide derivative synthesized in Step 1 is conjugated with a chelating agent in Step 2.

For this conjugation, the α-MSH peptide derivative synthesized in Step 1 is reacted with DOTA-mono-NHS-tris(tBu ester) in the presence of excess DIPEA in DMF as a solvent.

Instead of DOTA, other chelating agents may be used in the present invention.

Examples of the chelating agent useful in the present invention include DOTA, diethylene triaminepentaacetic acid (DTPA), 1,4,7-triazacyclononan-1,4,7-triacetic acid (NOTA), triethylene tetramine (TETA) or deferoxamine (DFO), with DOTA and DTPA being preferred.

Afterwards, the partial amino acid sequence Dap-Glu-His-dPhe-Arg-Trp-Asp (SEQ ID NO: 7) may be optionally subjected to cyclization by oxidizing the allyl group of Asp into a carboxyl group, followed by the formation of an amide bond with the $NH_2$ of Dap. In greater detail, the cyclization may be accomplished by converting the allyl group of Asp (O-Allyl) into a carboxyl group in the presence of tetrakis(triphenylphosphine)palladium in a mixture of 1,3-dimethylbarbituric acid and methyl chloride and reacting the carboxylic group with the $NH_2$ of Dap in a solution of DIC and HOAT in DMF, but is not limited thereto.

Finally, Step 3 is to remove a protecting group from the synthesized peptide derivative.

In this step, TFA, TIS, EDT, thioanisole and water are added so as to deprotect the peptide derivative synthesized in Step 2. For effective deprotection, TFA, TIS, EDT, thioanisole and water are preferably added at a ratio of TFA:TIS:EDT:thioanisole:water of 90~92:2.0~2.5:2.0~2.5:2.0~2.5:2.0~2.5.

Featuring high selectivity for melanocortin-1 receptor, a receptor for α-MSH expressed in melanoma (FIG. 7), an excellent radiolabeling rate of 98% or higher (FIGS. 2~5), a short renal retention time (FIG. 6) and a high tumor uptake, the chelating agent-conjugated α-MSH peptide derivative prepared according to the present invention is useful in the diagnosis and treatment of melanoma.

In accordance with a further aspect thereof, the present invention provides a radiolabeled chelating agent-conjugated α-MSH peptide derivative.

The radioisotopes used in the radiolabeled chelating agent-conjugated α-MSH peptide derivative according to the present invention include metal and transition metal ions, which can be detected with MRI, CT or a gamma camera, and radiation-emitting isotopes. For example, the radioisotope useful in the present invention may be selected from a group consisting of Sc-47, Cu-64, Cu-67, Ga-67, Ga-68, Y-86, Y-90, Tc-99m, In-111, Pm-149, Sm-153, Dy-165, Ho-166, Er-169, Lu-177, Re-186, Re-188 and Bi-212. Preferable is Lu-177 or Sm-153.

In accordance with still a further aspect thereof, the present invention provides a method for preparing the radiolabeled chelating agent-conjugated α-MSH peptide derivative of the present invention.

The radiolabeled chelating agent-conjugated α-MSH peptide derivative may be prepared by reacting the chelating agent-conjugated α-MSH peptide derivative of the present invention with a radioisotope in the presence of a stabilizer. The stabilizer may be selected from among ascorbic acid and dihydroxybenzoic acid.

In accordance with still another aspect thereof, the present invention provides a diagnostic composition for melanoma comprising the radiolabeled chelating agent-conjugated α-MSH peptide derivative of the present invention as an active ingredient.

In accordance with yet another aspect thereof, the present invention provides a composition for the treatment of melanoma comprising the radiolabeled chelating agent-conjugated α-MSH peptide derivative of the present invention as an active ingredient.

In accordance with still another aspect thereof, the present invention provides a method for diagnosis of melanoma, comprising administering radiolabeled chelating agent-conjugated α-MSH peptide derivative in an effective amount to a subject in need thereof.

In accordance with yet another aspect thereof, the present invention provides a method for treating melanoma, comprising administering radiolabeled chelating agent-conjugated α-MSH peptide derivative in a therapeutically effective amount to a subject in need thereof.

The radiolabeled chelating agent-conjugated α-MSH peptide derivative according to the present invention enjoys the advantage of being highly selective for a melanocortin-1 receptor, a receptor for α-MSH expressed in melanoma (FIG. 7), showing a radiolabeling rate of 98% or higher (FIGS. 2~5), staying in the kidney for a short time period (FIG. 6), and being high in tumor uptake (FIG. 7), so that it can be usefully applied to the diagnosis of melanoma with the aid of a medical imaging apparatus, and to the treatment of melanoma taking advantage of the energy emitted from the radioisotope.

The abbreviations used in the preceding description and the following examples are defined as follows: "Dap" stands for diaminopropionic acid, "MBHA" for methylbenzhydrylamine, "HOBT" for N-hydroxy-benzotriazole, "HBTU" for 2-(1H-Benzotriazole-1-yl)-1,1,3,3-tetramethyluronium hexafluorophosphate, "DIPEA" for diisopropylethylamine, "Fmoc" for 9-fluorenylmethyloxycarbonyl, "NHS" for N-hydroxysuccinimide, "DIC" for N,N-diisopropylcarbodiimide, "HOAT" for 1-hydroxy-7-azabenzotriazole, "TFA" for Trifluoroacetic acid, "TIS" for triisopropylsilane, "EDT" for ethane dithiol, "Boc" for tert-butyloxycarbonyl, "Pbf" for 2,2,4,6,7-pentamethyldihydrobenzofuran-5-sulfonyl, "Trt" for trityl, "DCM" for dichloromethane, and "DMF" for dimethylformamide.

A better understanding of the present invention may be obtained through the following examples, which are set forth to illustrate, but are not to be construed as the limit of the present invention.

Example 1

Preparation of DOTA-Gly-Dap-Glu-His-dPhe-Arg-Trp-Asp-CON $H_2$ (SEQ ID NO: 1)

(1) Peptide Synthesis $NH_2$-MBHA-resin was washed with DMF (N,N-dimethylformamide) and then with a 1.0 M HOBT solution in DMF. Afterwards, a DMF solution containing 3 equivalents of HOBt, 3 equivalents of HBTU, 6 equivalents of DIPEA and 3 equivalents of $N^\alpha$-Fmoc was added to the resin on which amino acid coupling reactions were then conducted for 2 hrs with stirring. The completeness of the amino acid coupling reactions was checked, as indicated by a negative result in a Kaiser test (E. Kaiser et al., Anal. Biochem. (1970) 34, 595). If the result was positive, the coupling reaction was repeated until a negative result of the Kaiser test was obtained. That is, the resin was washed with DMF and mixed with 3 equivalents of HOBt, 3 equivalents of HBTU, 6 equivalents of DIPEA and 3 equivalents of $N^\alpha$-Fmoc in DMF for 3 hrs with stirring. After the completion of the coupling reaction, the resin was washed with DMF and the N-terminal amino group of the peptide anchored to the resin was deprotected. For this, the peptide anchored to the resin was stirred in a mixture of 1:1 of a DMF solution containing 20% anhydrous acetic acid:a DMF solution containing 20% DIPEA for 10 min, followed by adding a DMF solution containing 20% piperidine and stirring the resin for 10 min to remove $N^\alpha$-Fmoc.

Subsequently, the resin was washed with DMF, DCM, and DMF in that order, followed by coupling reactions with $N^\alpha$-Fmoc protected amino acids in the order of Asp(O-tBu), Trp($N^i$-Boc), Arg(Ng-Pbf), D form-Phe, His($N^{im}$-Trt), Glu($N^\delta$-Trt), Dap(Boc), and Gly to synthesize a Gly-Dap-Glu-His-dPhe-Arg-Trp-Asp-CONH$_2$ (SEQ ID NO: 1) peptide.

(2) Conjugation with DOTA chelator

For the attachment of a DOTA chelator, a DMF solution containing 3 equivalents of DOTA-mono-NHS-tris(tBu ester) and 6 equivalents of DIPEA was added to the peptide synthesized in Example 1-(1) and stirred for 12 hrs. The peptide was deprotected and detached from the resin by reacting with a mixture of 90:2.5:2.5:2.5:2.5 TFA:TIS:EDT:thioanisole:water for 2 hrs, followed by precipitation in excess refrigerated diethyl ether. Excess TFA was primarily removed through centrifugation to collect the precipitate. This centrifugation process was repeated twice to afford a solid peptide.

The peptide was purified by HPLC on a C-19 column with a gradient of acetonitrile containing 0.01% TFA and between 5% and 100% of acetonitrile/water over 50 min. The purified fraction was freeze-dried to give the desired DOTA-Gly-Dap-Glu-His-dPhe-Arg-Trp-Asp-CONH$_2$ (SEQ ID NO: 1) as a white powder (yield: 10%).

Example 2

Preparation of DOTA-Gly-Dap-Glu-His-dPhe-Arg-Trp-Asp-Lys-Pro-Val-CONH$_2$ (SEQ ID NO: 2)

The same procedure as in Example 1 was repeated, with the exception that the amino acid coupling reactions were conducted in the order of $N^\alpha$-Fmoc-protected Val, Pro, Lys($N^\epsilon$-Boc), Asp(O-Allyl), Trp($N^i$-Boc), Arg(Ng-Pbf), Phe, His ($N^{im}$-Trt), Glu(Nδ-Trt), Dap(Alloc), and Gly, to prepare the desired DOTA-Gly-Dap-Glu-His-dPhe-Arg-Trp-Asp-Lys-Pro-Val-CONH$_2$ peptide (SEQ ID NO: 2) (yield: 10%).

Example 3

Preparation of DOTA-Gly-Dap-Glu-His-dPhe-Arg-Trp-Asp-Arg-Pro-Val-CONH$_2$ (SEQ ID NO: 3)

The same procedure as in Example 2 was repeated, with the exception that Arg was used instead of Lys, to prepare the desired DOTA-Gly-Dap-Glu-His-dPhe-Arg-Trp-Asp-Arg-Pro-Val-CONH$_2$ (SEQ ID NO: 3) (yield: 10%).

Example 4

Preparation of DOTA-Gly-Dap-Gln-His-dPhe-Arg-Trp-Asp-CON H$_2$ (SEQ ID NO: 4)

The same procedure as in Example 1 was repeated, with the exception that Gln was used instead of Glu, to prepare the desired DOTA-Gly-Dap-Gln-His-dPhe-Arg-Trp-Asp-CONH$_2$ (SEQ ID NO: 4) (Yield: 10%).

Example 5

Preparation of DOTA-Gly-Dap-Gln-His-dPhe-Arg-Trp-Asp-Lys-Pro-Val-CONH$_2$ (SEQ ID NO: 5)

The same procedure as in Example 2 was repeated, with the exception that Gln was used instead of Glu, to prepare the desired DOTA-Gly-Dap-Gln-His-dPhe-Arg-Trp-Asp-Lys-Pro-Val-CONH$_2$ (SEQ ID NO: 5) (Yield: 10%).

Example 6

Preparation of DOTA-Gly-Dap-Gln-His-dPhe-Arg-Trp-Asp-Arg-Pro-Val-CONH$_2$ (SEQ ID NO: 6)

The same procedure as in Example 3 was repeated, with the exception that Gln was used instead of Glu, to prepare the desired DOTA-Gly-Dap-Gln-His-dPhe-Arg-Trp-Asp-Arg-Pro-Val-CONH$_2$ (SEQ ID NO: 6) (Yield: 10%).

Example 7

Preparation of DOTA-Gly-cyclic(Dap-Glu-His-dPhe-Arg-Trp-Asp)-CONH$_2$ (1) Peptide Synthesis NH$_2$-MBHA-resin was washed with DMF (N,N-dimethylformamide) and then with a 1.0 M HOBT solution in DMF. Afterwards, a DMF solution containing 3 equivalents of HOBt, 3 equivalents of HBTU, 6 equivalents of DIPEA and 3 equivalents of $N^\alpha$-Fmoc was added to the resin, on which amino acid coupling reactions were then conducted for 2 hrs with stirring. The completeness of the amino acid coupling reactions was checked as indicated by a negative result of a Kaiser test. If a positive result was obtained, the coupling reaction was until a negative result of the Kaiser test was obtained. That is, the resin was washed with DMF and mixed with 3 equivalents of HOBt, 3 equivalents of HBTU, 6 equivalents of DIPEA and 3 equivalents of $N^\alpha$-Fmoc in DMF for 3 hrs with stirring. After the completion of the coupling reaction, the resin was washed with DMF and the N-terminal amino group of the peptide anchored to the resin was deprotected. For this, the peptide anchored to the resin was stirred in a mixture of 1:1 of a DMF solution containing 20% anhydrous acetic acid:a DMF solution containing 20% DIPEA for 10 min, followed by adding a DMF solution containing 20% piperidine and stirring the resin for 10 min to remove $N^\alpha$-Fmoc. Subsequently, the resin was washed with DMF, DCM, and DMF in that order, followed by coupling reactions with $N^\alpha$-Fmoc protected amino acids in the order of Asp(O-Allyl), Trp($N^i$-Boc), Arg(Ng-Pbf), D form-Phe, His($N^{im}$-Trt), Glu (N$^\delta$-Trt), Dap(Alloc), and Gly to synthesize a Gly-Dap-Glu-His-dPhe-Arg-Trp-Asp-CONH$_2$ (SEQ ID NO: 1) peptide.

(2) Conjugation with DOTA Chelator

For the attachment of a DOTA chelator, a DMF solution containing 3 equivalents of DOTA-mono-NHS-tris(tBu ester) and 6 equivalents of DIPEA was added to the peptide synthesized in Example 1-(1) and stirred for 12 hrs.

After the addition of a dichloromethane solution containing 0.2 equivalents of tetrakis(triphenylphosphine)palladium and 10 equivalents of 1,3-dimethylbarbituric acid to the resin, an oxidation reaction was conducted for 4 hrs. The resin was then washed with a 20% piperidine in DMF, methanol, and DMF in that order, so that the protecting groups Alloc for Dap and Allyl for Asp were removed to make the $NH_2$ of Dap and the COOH of Asp free.

Subsequently, a DMF solution containing 8 equivalents of DIC and 8 equivalents of HOAT was added to the peptide resin to perform a cyclization reaction to form an amide bond between the NH2 of Dap and the COOH of Asp.

Next, the peptide was deprotected and detached from the resin by reacting with a mixture of 90:2.5:2.5:2.5:2.5 TFA: TIS:EDT:thioanisole:water for 2 hrs, followed by precipitation in excess refrigerated diethyl ether. Excess TFA was primarily removed through centrifugation to collect the precipitate. This centrifugation process was repeated twice to afford a solid peptide.

The peptide was purified by HPLC on a C-19 column with a gradient of acetonitrile containing 0.01% TFA between 5% and 100% of acetonitrile/water in 50 min. The purified fraction was freeze-dried to give the desired DOTA-Gly-cyclic(Dap-Glu-His-dPhe-Arg-Trp-Asp)-$CONH_2$ as a white powder (yield: 10%).

Example 8

Preparation of DOTA-Gly-Cyclic(Dap-Glu-His-dPhe-Arg-Trp-Asp)-Lys-Pro-Val-$CONH_2$ The same procedure as in Example 7 was repeated, with the exception that the amino acid coupling reactions were conducted in the order of $N^\alpha$-Fmoc-protected Val, Pro, Lys($N^\epsilon$-Boc), Asp(O-Allyl), Trp($N^i$-Boc), Arg(Ng-Pbf), Phe, His ($N^{im}$-Trt), Glu($N^\delta$-Trt), Dap(Alloc) and Gly, to prepare the desired DOTA-Gly-cyclic(Dap-Glu-His-dPhe-Arg-Trp-Asp)-Lys-Pro-Val-$CONH_2$ peptide (yield: 10%).

Example 9

Preparation of DOTA-Gly-Cyclic(Dap-Glu-His-dPhe-Arg-Trp-Asp)-Arg-Pro-Val-$CONH_2$ The same procedure as in Example 8 was repeated, with the exception that Arg was used instead of Lys, to prepare the desired DOTA-Gly-Cyclic(Dap-Glu-His-dPhe-Arg-Trp-Asp)-Arg-Pro-Val-$CONH_2$ (Yield: 10%).

Example 10

Preparation of DOTA-Gly-Cyclic(Dap-Gln-His-dPhe-Arg-Trp-Asp)-$CONH_2$

The same procedure as in Example 7 was repeated, with the exception that Gln was used instead of Glu, to prepare the desired DOTA-Gly-cyclic(Dap-Gln-His-dPhe-Arg-Trp-Asp)-$CONH_2$ (Yield: 10%).

Example 11

Preparation of DOTA-Gly-Cyclic(Dap-Gln-His-dPhe-Arg-Trp-Asp)-Lys-Pro-Val-$CONH_2$ The same procedure as in Example 8 was repeated, with the exception that Gln was used instead of Glu, to prepare the desired DOTA-Gly-cyclic(Dap-Gln-His-dPhe-Arg-Trp-Asp)-Lys-Pro-Val-$CONH_2$ (Yield: 10%).

Example 12

Preparation of DOTA-Gly-Cyclic(Dap-Gln-His-dPhe-Arg-Trp-Asp)-Arg-Pro-Val-$CONH_2$ The same procedure as in Example 9 was repeated, with the exception that Gln was used instead of Glu, to prepare the desired DOTA-Gly-cyclic(Dap-Gln-His-dPhe-Arg-Trp-Asp)-Arg-Pro-Val-$CONH_2$ (Yield: 10%).

Example 13

Preparation of $^{177}$Lu-Labeled DOTA-Gly-cyclic(Dap-Glu-His-dPhe-Arg-Trp-Asp)-Lys-Pro-Val-CON $H_2$ To 1 M sodium acetate buffer (pH 5.0) was added 1 g of the DOTA-Gly-cyclic(Dap-Glu-His-dPhe-Arg-Trp-Asp)-Lys-Pro-Val-$CONH_2$ prepared in Example 11, and 100 μg of the solution was reacted with 1 mCi of $^{177}LuCl_3$ at 90° C. for 30 min in the presence of 50 mg of ascorbic acid and 6 mg of dihydroxybenzoic acid as a stabilizer in a vial. After completion of the reaction, it was chilled in an ice water bath.

Peptide labeling was monitored by a TLC plate (ITLC-SG) with saline as a mobile phase, and then analyzed using a Cyclone. The results are depicted in FIG. 1.

As shown in FIG. 1, $^{177}LuCl_3$ migrated with the solvent front Rf0.9~1.0 and the labeled peptide migrated from the origin Rf=0~0.1.

Also, the radiolabeled ligand was analyzed by HPLC on a C-18 reverse-phase X-Terra (5 μm, 4×250 mm) column with a gradient of water (A) and acetonitrile (B) containing 0.1% trifluoroacetic acid at a flow rate of 1 m/min (A: solvent flow condition: 100~90% 2 min; 90~60% 10 min; 60~30% 2 min; 30~3 min; and 30~100% 3 min).

Figure 2:
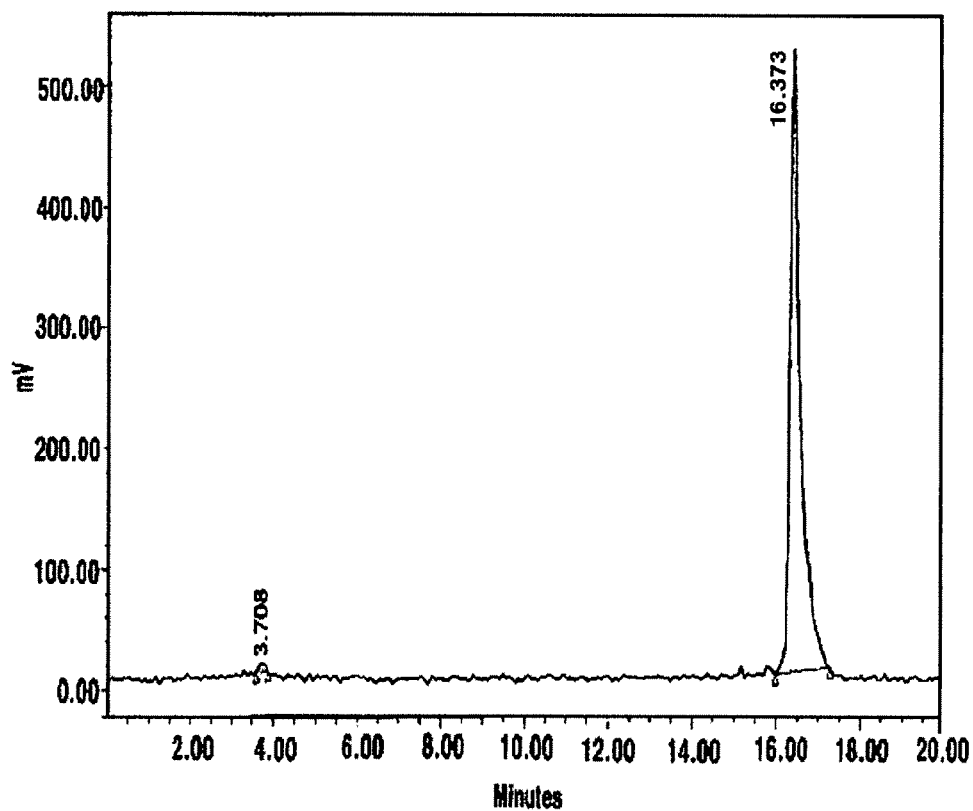
FIG. 2 is an HPLC chromatogram of a radiolabeled chelating agent-conjugated α-MSH peptide derivative according to an embodiment of the present invention.

The analysis result is given in FIG. 2.

As shown in the chromatogram of FIG. 2, the $^{177}$Lu-labeled DOTA-Gly-cyclic(Dap-Glu-His-dPhe-Arg-Trp-Asp)-Lys-Pro-Val-$CONH_2$ according to the present invention was prepared at a radiolabeling rate of 99% or higher.

Example 14

Preparation of $^{153}$Sm-Labeled DOTA-Gly-cyclic(Dap-Glu-His-dPhe-Arg-Trp-Asp)-Lys-Pro-Val-CON $H_2$ The same procedure as in Example 13 was repeated, with the exception that $^{153}$Sm, instead of $^{177}LuCl_3$, was used in an amount of 1 mCi.

Labeling yield was analyzed in the same HPLC process as in Example 13 ((A) solvent flow condition: 90~50% 10 min; 50~30% 2 min; 30% 1 min; and 30~90% 1 min).

Figure 3:
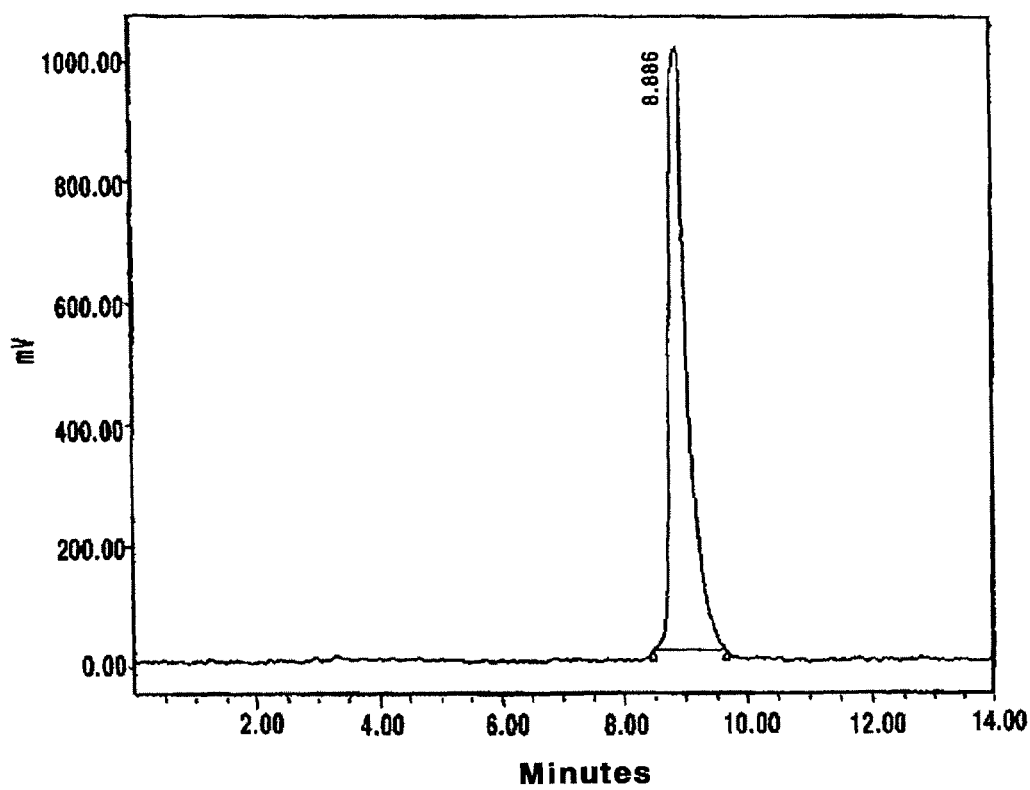
FIG. 3 is an HPLC chromatogram of a radiolabeled chelating agent-conjugated α-MSH peptide derivative according to an embodiment of the present invention.

Analysis results are shown in FIG. 3.

As shown in the chromatogram of FIG. 3, the $^{153}$Sm-labeled DOTA-Gly-cyclic(Dap-Glu-His-dPhe-Arg-Trp-Asp)-Lys-Pro-Val-$CONH_2$ of the present invention was prepared at a labeling yield of 100%.

Example 15

Preparation of $^{153}$Sm-Labeled DOTA-Gly-cyclic(Dap-Glu-His-dPhe-Arg-Trp-Asp)-Arg-Pro-Val-CON $H_2$ The same procedure as in Example 14 was repeated, with the exception that the DOTA-Gly-cyclic(Dap-Glu-His-dPhe- Arg-Trp-Asp)-Arg-Pro-Val-CONH$_2$ synthesized in Example 9 was used instead of DOTA-Gly-cyclic(Dap-Glu-His-dPhe-Arg-Trp-Asp)-Lys-Pro-Val-CONH$_2$. Analysis results are shown in FIG. 4.

Figure 4:
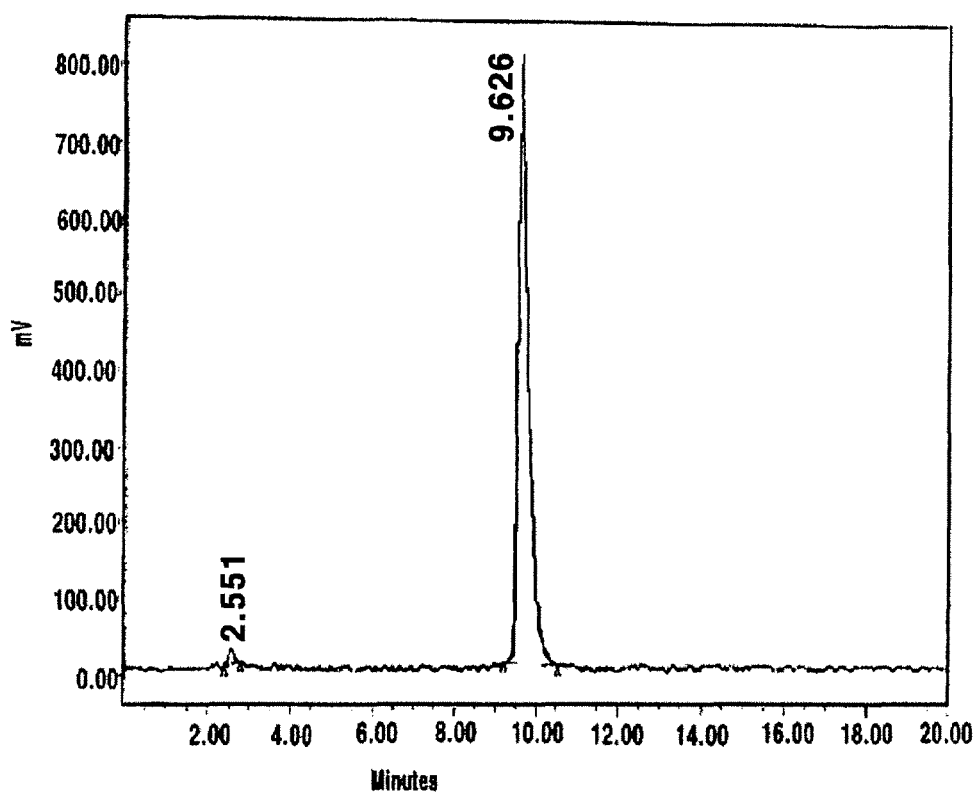
FIG. 4 is an HPLC chromatogram of a radiolabeled chelating agent-conjugated α-MSH peptide derivative according to an embodiment of the present invention.

As shown in the chromatogram of FIG. 4, the $^{153}$Sm-labeled DOTA-Gly-cyclic(Dap-Glu-His-dPhe-Arg-Trp-Asp)-Arg-Pro-Val-CONH$_2$ was prepared at a labeling yield of 100%.

Example 16

Preparation of $^{153}$Sm-Labeled DOTA-Gly-cyclic (Dap-Glu-His-dPhe-Arg-Trp-Asp)-CON H$_2$ The same procedure as in Example 14 was repeated, with the exception that the DOTA-Gly-cyclic(Dap-Glu-His-dPhe-Arg-Trp-Asp)-CONH$_2$ synthesized in Example 7 was used instead of DOTA-Gly-cyclic(Dap-Glu-His-dPhe-Arg-Trp-Asp)-Lys-Pro-Val-CONH$_2$. Analysis results are shown in FIG. 5.

Figure 5:
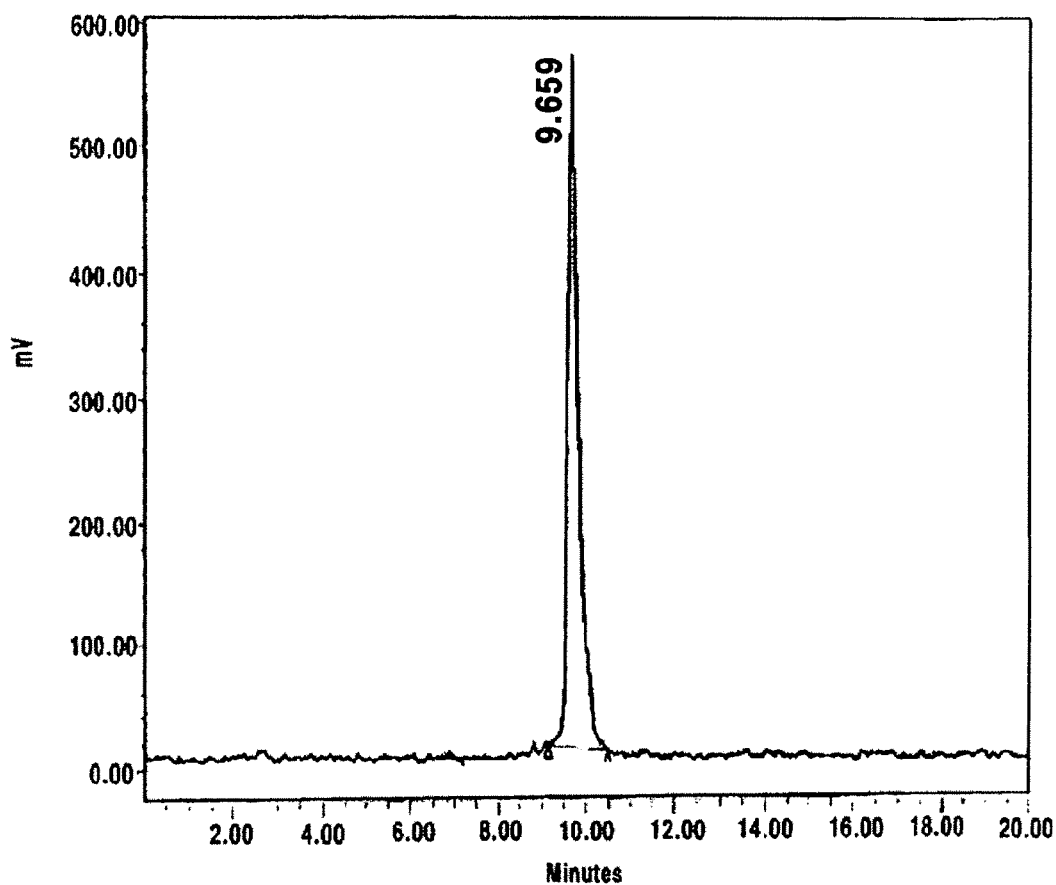
FIG. 5 is an HPLC chromatogram of a radiolabeled chelating agent-conjugated α-MSH peptide derivative according to an embodiment of the present invention.

As shown in the chromatogram of FIG. 5, the $^{153}$Sm-labeled DOTA-Gly-cyclic(Dap-Glu-His-dPhe-Arg-Trp-Asp)-CONH$_2$ was prepared at a labeling yield of 98%.

Experimental Example

Internal Dose Assessment

The selectivity of the peptides of the present invention for melanoma tumors was examined as follows.

(1) Internal Dose Assessment in Normal Animal

Internal dose assessment was conducted with the $^{177}$Lu-DOTA-Gly-Cyclic(Dap-Gln-His-dPhe-Arg-Trp-Asp)-Lys-Pro-Val-CONH$_2$ prepared in Example 13 in normal animals.

Nine normal Balb/C mice were acclimated to the new environment for 1 week before the injection of 20 µCi of the prepared radio ligand into their tail veins. The mice were sacrificed 2, 4 and 24 hours after the injection and subjected to ventrotomy to excise organs therefrom. The organs were analyzed for radioactivity using a gamma counter (1470 WIZARD Automatic Gamma Counter, PerkinElmer) and the results are graphed in FIG. 6.

Figure 6:
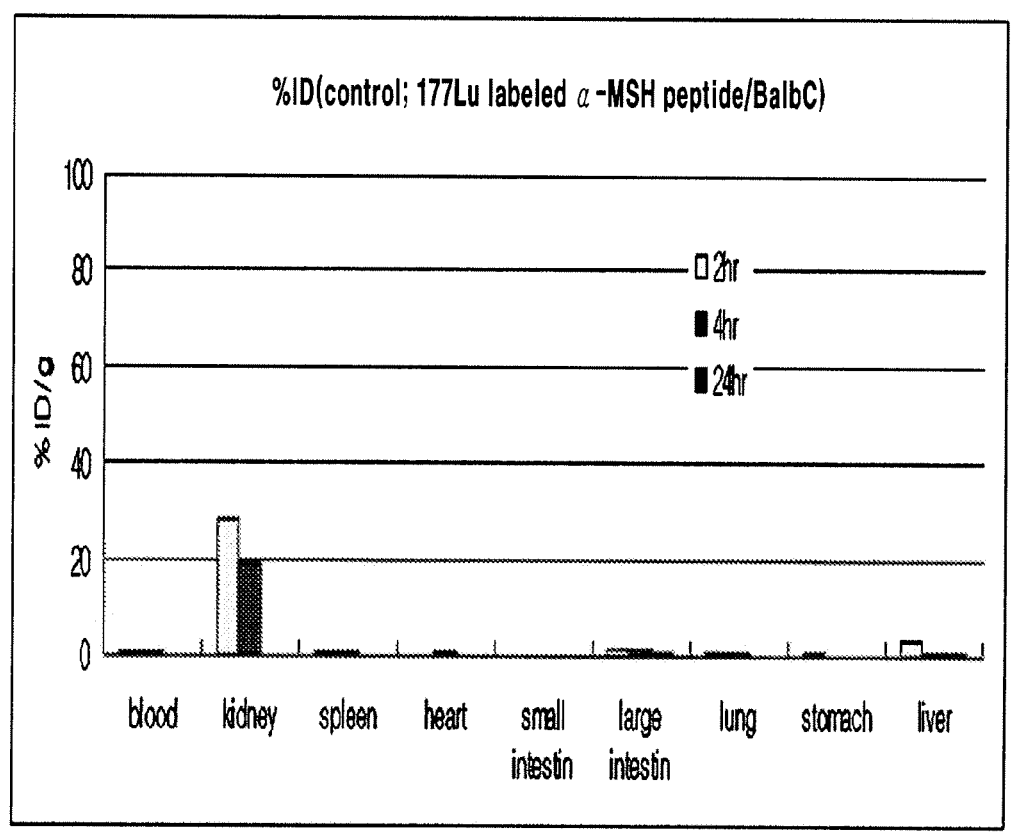
FIG. 6 is a histogram showing radioactivity levels in various organs of normal animals injected with a radiolabeled chelating agent-conjugated α-MSH peptide derivative according to an embodiment of the present invention.

AS seen in FIG. 6, the radioactivity was detected to be the highest in the kidney 2 hrs after the injection, but was decreased 4 hrs after the injection. No radioactivity was detected in the kidney excised 24 hrs after the injection. From these results, it is apparent that the peptide according to the present invention is excreted through the urinary system. Most of the radiolabeled compound was discharged from the body, as no radioactivity remained in the body 24 hrs after the injection.

(2) Internal Dose Assessment in Tumor Animal

To the nape of the neck of 12 female C57BL mice, each weighing 18~23 g, B16/F1 murine melanoma cells were injected at a density of 10$^6$ cells/mL. Two weeks later, the tumor was developed to a size of 0.5~1 g. The $^{177}$Lu-DOTA-Gly-Cyclic(Dap-Gln-His-dPhe-Arg-Trp-Asp)-Lys-Pro-Val-CONH$_2$ prepared in Example 13 was injected to the mice at a dose of 5 µCi (1.6 µg in 100 µl of saline). 2, 4 and 24 hours later, the mice were sacrificed before organ excision.

For comparison for target selectivity, the mice that were injected with 2 µg of an unlabeled peptide 2 hours after the first injection and then with the radiolabeled peptide were used as a control.

Figure 7:
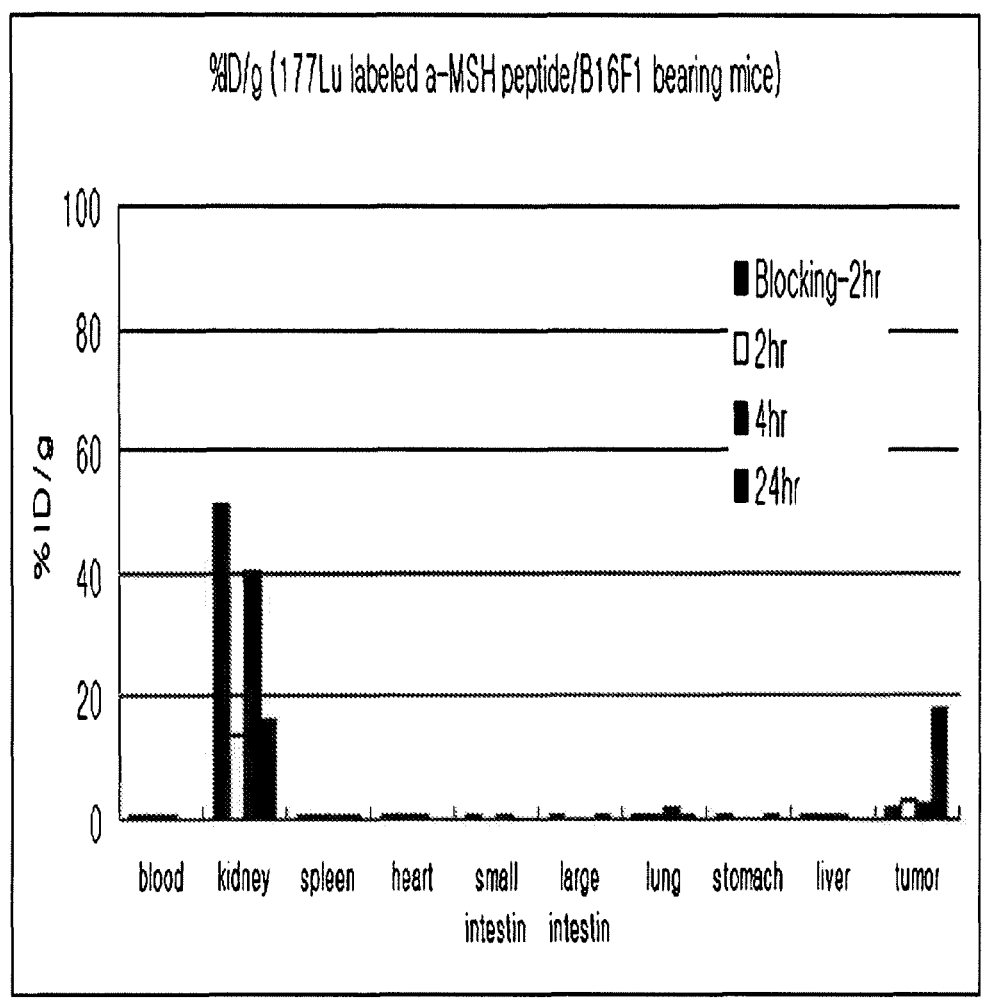
FIG. 7 is a histogram showing radioactivity levels in various organs of tumorous animals injected with a radiolabeled chelating agent-conjugated α-MSH peptide derivative according to an embodiment of the present invention.

The excised organs were analyzed for radioactivity using a gamma counter (1470 WIZARD Automatic Gamma Counter, PerkinElmer) and the results are plotted in FIG. 7.

As seen in FIG. 7, the peptide according to the present invention was observed to be deposited in the tumor starting 2 hrs after injection. Under the same conditions, the control showed lower tumor uptake than did the experimental groups. These results indicate that the peptide compound of the present invention has high receptor selectivity. Also, it was observed that the tumor uptake of the peptide according to the present invention increased 24 hrs after the injection.

Therefore, the peptides of the present invention can be effectively used as radiocontrast agents for the diagnosis and treatment of melanoma.

As described hitherto, having the advantage of being highly selective for a melanocortin-1 receptor, a receptor for α-MSH expressed in melanoma (FIG. 7), showing an excellent radiolabeling rate, staying in the kidney for a short time period, and being high in tumor uptake, the radiolabeled chelating agent-conjugated α-MSH peptide derivative according to the present invention can be usefully applied in the diagnosis and treatment of primary melanoma.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A chelating agent-conjugated α-MSH (melanocyte stimulating hormone) peptide derivative, wherein the α-MSH peptide derivative is an amino acid sequence selected from a group consisting of:

1) Gly-Dap-Glu-His-dPhe-Arg-Trp-Asp-CONH$_2$; (SEQ ID NO: 1)

2) Gly-Dap-Glu-His-dPhe-Arg-Trp-Asp-Lys-Pro-Val-CONH$_2$; (SEQ ID NO: 2)

3) Gly-Dap-Glu-His-dPhe-Arg-Trp-Asp-Arg-Pro-Val-CONH$_2$; (SEQ ID NO: 3)

4) Gly-Dap-Gln-His-dPhe-Arg-Trp-Asp-CONH$_2$; (SEQ ID NO: 4)

5) Gly-Dap-Gln-His-dPhe-Arg-Trp-Asp-Lys-Pro-Val-CONH$_2$; and (SEQ ID NO: 5)

6) Gly-Dap-Gln-His-dPhe-Arg-Trp-Asp-Arg-Pro-Val-CONH$_2$. (SEQ ID NO: 6)

2. The chelating agent-conjugated α-MSH peptide derivative according to claim 1, wherein a chelating agent selected from a group consisting of 1,4,7,10-tetrazacyclododecane-1,4,7,10-tetraacetic acid (DOTA) and diethylenetriaminepentaacetic acid (DTPA).

3. The chelating agent-conjugated α-MSH peptide derivative according to claim 1, wherein a partial amino acid sequence -Dap-Glu-His-dPhe-Arg-Trp-Asp- (SEQ ID NO:7) of (SEQ ID NO:1), (SEQ ID NO:2), or (SEQ ID NO:3) or a partial amino acid sequence Dap-Gln-His-dPhe-Arg-Trp-Asp- of (SEQ ID NO:4), (SEQ ID NO:5), or (SEQ ID NO:6) is in a straight form or a cyclic form.

4. A method for preparing a chelating agent-conjugated α-MSH peptide derivative of claim 1, comprising:
synthesizing the α-MSH peptide derivative through amino acid coupling reactions wherein the amino acid coupling reactions are performed on NH$_2$-MBHA (methylbenzhydrylamine) resin with excess HOBt (N-hydroxybenzotriazole), excess HBTU (2-(1-H-Benzotriazole-1-yl)-1,1,3,3-tetramethyluronium), excess DIPEA (diisopropylethylamine) and excess N$^\alpha$-Fmoc (9-fluorenylmethyloxycarbonyl) in a DMF (dimethylformamide) solvent;
conjugating the α-MSH peptide derivative with a chelating agent to form a conjugate; and
deprotecting the conjugate.

5. The method according to claim 4, wherein the conjugating is accomplished by reacting the α-MSH peptide derivative with DOTA-mono-NHS-tris(tBu ester) in the presence of excess DIPEA in a DMF solvent.

6. A radiolabeled chelating agent-conjugated α-MSH peptide derivative, wherein the chelating agent-conjugate α-MSH peptide derivative of claim 1 is labeled with a radioisotope.

7. The radiolabeled chelating agent-conjugated α-MSH peptide derivative according to claim 6, wherein the radioisotope is selected from a group consisting of Sc-47, Cu-64, Cu-67, Ga-67, Ga-68, Y-86, Y-90, Tc-99m, In-111, Pm-149, Sm-153, Dy-165, Ho-166, Er-169, Lu-177, Re-186, Re-188 and Bi-212.

8. A method for preparing the radiolabeled chelating agent-conjugated α-MSH peptide derivative of claim 5, comprising reacting the chelating agent-conjugated α-MSH peptide derivative with a radioisotope in the presence of a stabilizer.

9. The method according to claim 8, wherein the stabilizer is selected from a group consisting of ascorbic acid, dihydroxybenzoic acid and a combination thereof.

10. A method for diagnosis of melanoma, comprising administering a radiolabeled chelating agent-conjugated α-MSH peptide derivative of claim 6 in an effective amount to a subject in need thereof.

11. A method for treating melanoma, comprising administering a radiolabeled chelating agent-conjugated α-MSH peptide derivative of claim 8 in a therapeutically effective amount to a subject in need thereof.

* * * * *

UNITED STATES PATENT AND TRADEMARK OFFICE
CERTIFICATE OF CORRECTION

PATENT NO. : 8,124,054 B2  
APPLICATION NO. : 12/409288  
DATED : February 28, 2012  
INVENTOR(S) : Hong et al.

Page 1 of 1

It is certified that error appears in the above-identified patent and that said Letters Patent is hereby corrected as shown below:

IN THE CLAIMS:

Column 18, In Claim 8, line 2, please delete "claim 5" and replace with --claim 6--.

Column 18, In Claim 11, line 3, please delete "claim 8" and replace with --claim 6--.

Signed and Sealed this  
Twenty-second Day of May, 2012

David J. Kappos  
*Director of the United States Patent and Trademark Office*

UNITED STATES PATENT AND TRADEMARK OFFICE
CERTIFICATE OF CORRECTION

PATENT NO. : 8,124,054 B2  
APPLICATION NO. : 12/409288  
DATED : February 28, 2012  
INVENTOR(S) : Hong et al.

Page 1 of 1

It is certified that error appears in the above-identified patent and that said Letters Patent is hereby corrected as shown below:

IN THE CLAIMS:

Column 18, line 54 (Claim 8, line 2) please delete "claim 5" and replace with --claim 6--.

Column 18, line 65 (Claim 11, line 3) please delete "claim 8" and replace with --claim 6--.

This certificate supersedes the Certificate of Correction issued May 22, 2012.

Signed and Sealed this  
Nineteenth Day of June, 2012

David J. Kappos  
*Director of the United States Patent and Trademark Office*